US011124471B2

(12) United States Patent
Lygin et al.

(10) Patent No.: US 11,124,471 B2
(45) Date of Patent: Sep. 21, 2021

(54) PROCESS FOR OXIDATIVE ESTERIFICATION OF ALDEHYDES TO CARBOXYLIC ACID ESTERS

(71) Applicant: Roehm GmbH, Darmstadt (DE)

(72) Inventors: Alexander Lygin, Griesheim (DE); Steffen Krill, Muehltal (DE); Belaid Ait Aissa, Darmstadt (DE); Florian Zschunke, Frankfurt (DE)

(73) Assignee: Roehm GmbH, Darmstadt (DE)

( * ) Notice: Subject to any disclaimer, the term of this patent is extended or adjusted under 35 U.S.C. 154(b) by 14 days.

(21) Appl. No.: 16/611,546

(22) PCT Filed: Apr. 23, 2018

(86) PCT No.: PCT/EP2018/060255

§ 371 (c)(1),
(2) Date: Nov. 7, 2019

(87) PCT Pub. No.: WO2018/206276

PCT Pub. Date: Nov. 15, 2018

(65) Prior Publication Data

US 2021/0047259 A1 Feb. 18, 2021

(30) Foreign Application Priority Data

May 9, 2017 (EP) .................................... 17170111

(51) Int. Cl.
*C07C 67/39* (2006.01)
*B01J 23/52* (2006.01)
*C07C 69/54* (2006.01)

(52) U.S. Cl.
CPC ............... *C07C 67/39* (2013.01); *B01J 23/52* (2013.01); *C07C 69/54* (2013.01)

(58) Field of Classification Search
CPC ......... C07C 67/39; C07C 69/54; C07C 67/54; B01J 23/52; B01J 2208/00017; B01J 2208/00539; B01J 2219/00033; Y02P 20/584
See application file for complete search history.

(56) References Cited

U.S. PATENT DOCUMENTS 5,969,178 A 10/1999 Okamoto et al.
8,450,235 B2 * 5/2013 Suzuki .................. B01J 35/008 502/325
2016/0068464 A1 3/2016 Krill et al.
2016/0200660 A1 * 7/2016 Krill ...................... C07C 45/75 560/208
2016/0280628 A1 * 9/2016 Krill ...................... C07C 45/75
2018/0050977 A1 2/2018 Krill et al.

FOREIGN PATENT DOCUMENTS

EP 2 886 529 A1 6/2015
EP 2886529 * 6/2015
WO WO 2014/170223 A1 10/2014
WO WO2015/043861 * 4/2015

OTHER PUBLICATIONS

International Search Report dated Jul. 3, 2018 in PCT/EP2018/060255 filed on Apr. 23, 2018.

* cited by examiner

*Primary Examiner* — Jafar F Parsa
*Assistant Examiner* — Blaine G Doletski
(74) *Attorney, Agent, or Firm* — Oblon, McClelland, Maier & Neustadt, L.L.P.

(57) ABSTRACT

The present invention relates to a novel process for performing a heterogeneously catalyzed reaction for oxidative esterification of aldehydes to give carboxylic esters. Against this background, it has been possible by the present process according to the invention to perform such processes for longer periods without disruption, with constant or even increased activities and selectivities. This gives rise to the possibility of performing such processes in a very simple, economically viable and environmentally benign manner.

16 Claims, 1 Drawing Sheet

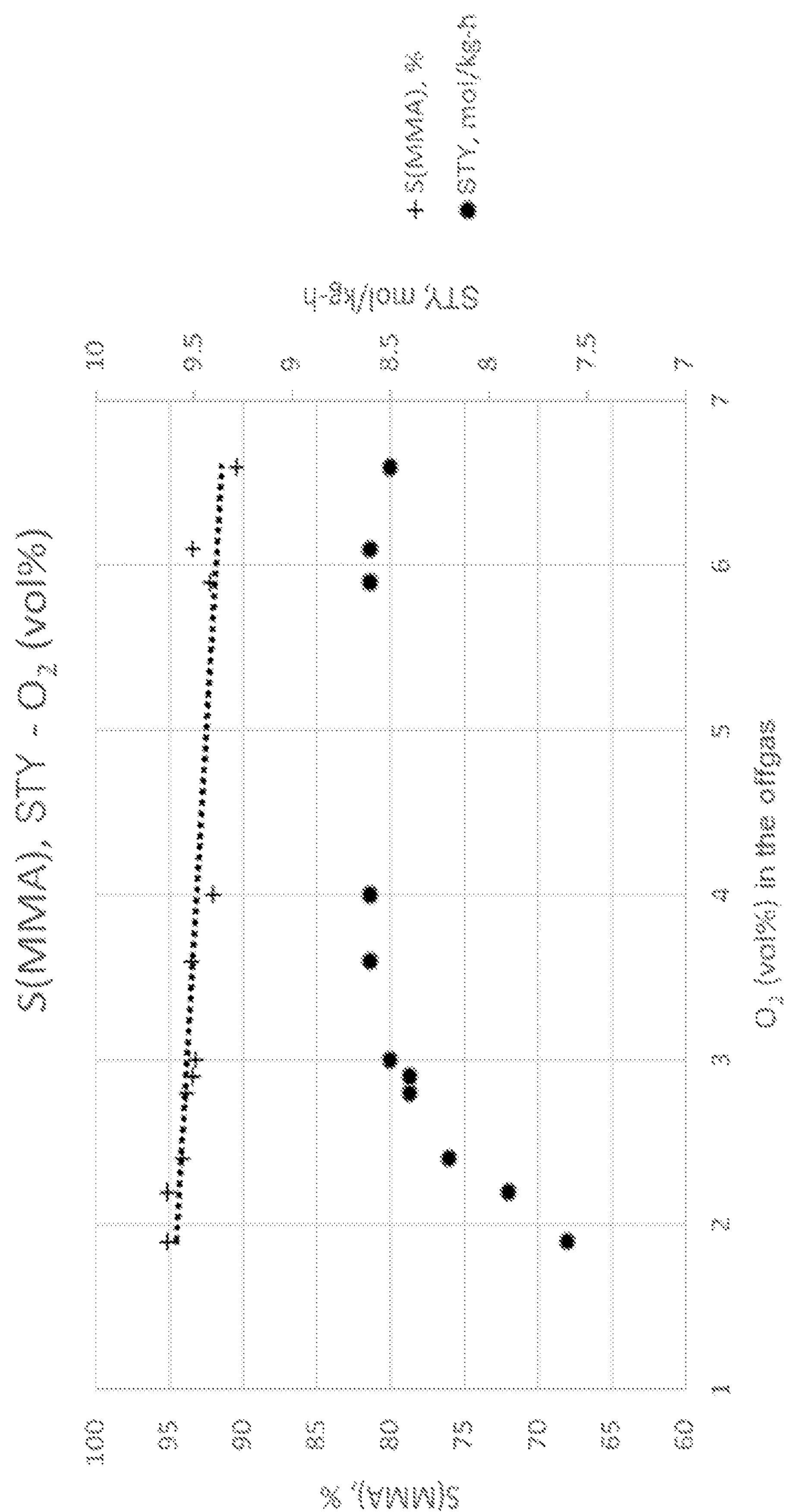
S(MMA), STY - $O_2$ (vol%)
S(MMA), %
100
95
90
85
80
75
70
65
60
STY, mol/kg-h
10
9.5
9
8.5
8
7.5
7
1
2
3
4
5
6
7
$O_2$ (vol%) in the offgas
S(MMA), %
STY, mol/kg-h

PROCESS FOR OXIDATIVE ESTERIFICATION OF ALDEHYDES TO CARBOXYLIC ACID ESTERS

FIELD OF THE INVENTION

The present invention relates to a novel process for performing a heterogeneously catalyzed reaction for oxidative esterification of aldehydes to give carboxylic esters.

Against this background, it has been possible by the present process according to the invention to perform such processes for longer periods without disruption, with constant or even increased activities and selectivities. This gives rise to the possibility of performing such processes in a very simple, economically viable and environmentally benign manner.

PRIOR ART

The catalytic oxidative esterification of aldehydes for preparation of carboxylic esters is described in numerous patents and references. For example, it is possible to prepare methyl methacrylate very efficiently from methacrolein and methanol.

When the readily polymerizable reactants and/or products are used or prepared, it is particularly important, for an economically viable process, to suppress polymerization as far as possible in order to achieve the high activities, selectivities and catalyst on-stream times. Particularly in the case of the costly precious metal catalyst based, for example, on Au, Pd, Ru or Rh, the catalyst on-stream time plays a crucial role. In the case of oxidative esterification of methacrolein (MAL) to methyl methacrylate (MMA), it is also desirable that the reaction can be conducted in the presence of relatively high MAL concentrations.

The prior art to date has not sufficiently described how a high catalyst activity, selectivity and long on-stream time can be implemented without deactivation and at high MAL concentrations in the reaction mixture.

The process for the direct oxidative esterification of methacrolein to MMA has been described many times before. For example, U.S. Pat. No. 5,969,178 describes a Pd-Pb-catalyzed conversion of MAL to MMA with a selectivity of 86.4% at a space-time yield (STY) of 5.5 mol of MMA/kg cat.*h. The possible MAL and methanol concentrations in the feed at the reactor inlet are discussed in detail here, but no information is given as to the composition in the reactor. The oxygen concentration in the reactor offgas is described and discussed with the following background: for instance, the oxygen concentration in the offgas, owing to the explosion limit, is to be less than 8% by volume. In addition, a smaller oxygen concentration in the reactor, and also in the offgas, is said to be disadvantageous for the reaction rate. Thus, excessively small oxygen concentrations led to increased formation of by-products.

On the other hand, however, it is also pointed out that the greater the oxygen concentration, the more Pb salts have to be fed continuously to the reactor in order that the catalyst performance remains constant and good.

The use range preferred for all these reasons for a Pd—Pb catalyst is thus between the partial oxygen pressure in the offgas of 0.01 and 0.8 kg/cm$^2$ with total pressure between 0.5 and 20 kg/cm$^2$. In the best embodiment of U.S. Pat. No. 5,969,178 of working example 1, the reaction is conducted at total pressure 3.0 kg/cm$^2$ and partial $O_2$ pressure 0.095 kg/cm$^2$ in the offgas (corresponding to 3.2 mol %).

U.S. Pat. No. 8,450,235 disclosed the use of an NiO/Au-based catalyst at total pressure 0.5 MPa and 4% by volume of oxygen in the offgas. The selectivity for MMA was 97.2%; the space-time yield was 9.57 mol of MMA/kg cat.*h. The molar ratio of methanol to methacrolein in the feed was 4.36 (mol/mol). The calculated corresponding ratio in the reactor was 14.7 (mol/mol).

If a distillative removal of methanol and methacrolein is to take place after the oxidative esterification, as described, for example, in U.S. Pat. No. 5,969,178, it is energetically more advantageous to reduce the molar ratio of methanol to methacrolein in the reactor to less than 10 (mol/mol). In this case, it is possible to remove more methanol as a low-boiling azeotrope of methanol and methacrolein. Advantageously, less MMA is included here in the recycle stream. The methanol-MAL azeotrope, according to U.S. Pat. No. 5,969,178, has a boiling point of 58° C. and a composition of methanol to MAL of 72.2% by weight to 27.7% by weight. The molar ratio of methanol to MAL here is 5.7.

As clearly shown by the examples below, if an attempt is made to conduct the experiments similarly to U.S. Pat. No. 8,450,235B2 (with 4% by volume of O2 in the offgas) with a MeOH/MAL ratio of less than 10, there is a severe deterioration in the activity and selectivity of the catalyst used within a short time.

A further problem in the performance of the oxidative esterification of Mal to MMA is that the volatile reactants (MAL and MeOH) are partly lost via the offgas, even in the case of intense cooling, which minimizes the overall yield.

The reduction of $O_2$ concentration in the offgas thus also has an additional advantage of reducing the losses of material of value via the offgas.

Problem

In view of the prior art, the problem addressed by the present invention is therefore that of providing a technically improved process for performing a heterogeneously catalyzed oxidative esterification reaction. This novel process is especially to be afflicted with fewer disadvantages than conventional prior art processes.

More particularly, prior art processes are to be improved in such a way that there is only minimal catalyst consumption, thus enabling a long on-stream time of the heterogeneous catalyst used with simultaneously good and virtually constant catalyst activity, selectivity and good mixing in the reactor.

Furthermore, the process, in the case of use of readily polymerizable reactants and formation of such products and/or by-products, is to enable such a reactor design that it permits only very minor polymerization at most.

Moreover, the process is to be inexpensive compared to the prior art, especially to be performable without any great catalyst losses as a result of abrasion or discharge, and is to implementable with fewer and shorter interruptions to operation. In addition, the process is especially to be reliably operable. For this purpose, explosive or excessively reactive compositions are to be very substantially avoided within the process.

Moreover, it should be possible to perform the process with relatively simple and inexpensive plants. The plants should accordingly be associated with low capital costs. At the same time, the plants should be simple to maintain, incur low maintenance costs and be operable safely.

Further objects not mentioned explicitly will become apparent from the overall context of the following description and the claims.

Solution

These problems are solved through the provision of a novel process for continuously performing a reaction—for example a heterogeneously catalyzed reaction—for oxidative esterification of methacrolein with an alkyl alcohol and oxygen to give an alkyl methacrylate in a reactor system consisting of one or more reactors, in the presence of a gold catalyst, wherein the reactor has at least one gas feed and at least one offgas outlet. This novel process is characterized in that the molar ratio between the steady-state concentrations of the alkyl alcohol and of the methacrolein in the reactor or within the individual reactors in the reactor system is less than 15:1, especially less than 10:1, in that the oxygen concentration in the gas phase within the reactor, or within the individual reactors of the reactor system, at the site of the offgas outlet is below the explosion limit of the exiting gas mixture or less than 7% by volume, in that the steady-state molar ratio of alkyl alcohol to methacrolein within the reactor, or within the individual reactors of the reactor system, to the molar ratio of the substances in the feed in the steady state is between 1.5 and 15, and in that the steady-state concentration of methacrolein within the reactor, or within the individual reactors of the reactor system, is less than 21% by weight.

It has been found by means of this novel process that, surprisingly, the continuous performance of an oxidative esterification, catalyzed by gold catalysts, of methacrolein to an alkyl methacrylate, such as, more particularly, to give MMA, with a ratio of the concentrations of the alkyl alcohol to methacrolein (MAL hereinafter) $C_{MeOH}/C_{MAL}$ of less than 10:1 (mol/mol) in the reaction mixture, is possible for a long period with high catalyst activity, selectivity and without technical faults when the oxygen concentration in the offgas is adjusted to less than 4% by volume of $O_2$. A good catalyst performance is achieved here, for example in relation to yield, selectivity and very high on-stream times, and additionally only the minimum amount of volatile substances of value is lost, such as the alkyl alcohol, especially methanol, MAL or others.

A crucial factor for the reaction, according to the invention, is the comparatively small proportion of oxygen in the gas phase in the reactor, or in the reactors. However, the oxygen content in this gas phase varies locally as a function of various factors within the reactor, or in the reactors. For instance, the concentration is naturally at its highest at the site of the feed of the oxygenous gas, for example air, while this concentration is naturally lower at other sites in the respective reactor, especially when the gas phase at that point has already been in prolonged contact with the reactants and the catalyst. This local distribution depends upon factors including the exact reactor architecture and the exact flow profile thereof. The total size of the interface between liquid and gaseous phases in the respective reactor also plays a role, as does the residence time of the gas phase in the continuously operated reactor. Therefore, it is actually possible to give only a poor description of the gas concentrations in the individual reactor. However, an exception is the removal of the offgas. For each reactor, irrespective of its architecture, the interfaces, the residence time, the partial pressures established, the total gas volume in the reactor or the flow profile, this value is unambiguously determinable and is generally a very good measure for the amount of oxygen used overall in a process. Depending on the construction and the fill level of a reactor with solid and liquid phases, the person skilled in the art is additionally able to adjust this value in a simple manner via the adjustment of the internal pressure and the feed rate of the oxygenous gas. The oxygen concentration can then be detected in the reactor directly at the removal point of the oxygen with sensors known for the purpose. Alternatively, it is also possible to determine the concentration in the first piece of the exhaust gas conduit, in that the total pressure and the temperature here deviate from the conditions in the reactor, if at all, only to a degree known to the person skilled in the art for a determination of a gas composition. After being withdrawn from the reactor, the offgas mixture is no longer reactive and the concentration can correspondingly be determined here too without any problem.

More preferably, the oxygen concentration in the gas phase within the reactor or in the reactors at the particular point at which offgas is withdrawn is less than 4.5% by volume, most preferably less than 4% by volume.

The steady-state molar ratio of alkyl alcohol to methacrolein within the reactor, or in the reactors, to the molar ratio of the substances in the feed in the steady state is preferably between 1.8 and 15. This factor is more preferably between 1.9 and 14, most preferably between 2 and 13. This feature reflects the conversion rate in the steady state of the reaction. Through the controlled adjustment of this factor, it is possible to optimize the yield of the reaction surprisingly well.

The steady-state concentration of methacrolein in the reactor, or in the reactors, is preferably less than 15% by weight, more preferably less than 12% by weight. In the reaction procedure according to the invention, particularly optimal results are obtained when the steady-state methacrolein concentration in the reactor is kept comparatively low.

In one variant of the reaction, it is entirely possible to conduct the reaction in two or more reactors connected in series. In this case, the features according to the invention, especially parameters, relate to the feed upstream of the first reactor in each case and the internal steady-state concentration of the last reactor in each case.

Preferably, in the process according to the invention, a catalyst in the form of catalyst particles is used. These particles preferably include the elements oxygen, silicon, aluminium, at least one basic element, gold, and optionally preferably at least one of the elements nickel, cobalt, iron and zinc. The basic elements listed may be an alkali metal, an alkaline earth metal, a rare earth metal or mixtures of these metals. The basic elements are especially an alkali metal (Li, Na, K, Rb, Cs, Fr), an alkaline earth metal (Be, Mg, Ca, Sr, Ba), a rare earth metal (Sc, Y, La, Ce, Pr, Nd, Pm, Sm, Eu, Gd, Tb, Dy, Ho, Er, Tm, Yb, Lu) or mixtures of these metals. The basic element is generally also present in oxide form.

Most preferably, the catalyst particle consists exclusively of gold and the oxides of silicon, of aluminium and of cobalt and of at least one of the basic elements. One example of a particularly suitable composition includes $SiO_2$, $Al_2O_3$, $Co_3O_4$, MgO and Au, especially exclusively these compounds. In addition, the catalyst particles of the invention are characterized in that the maximum gold concentration or the maximum iron, zinc or cobalt concentration of the catalyst particle is to be found in the outer region thereof. Said outer region makes up a maximum of 60%, preferably a maximum of 40% and more preferably a maximum of 30% of the geometric equivalent diameter of the catalyst particle. In this context, the gold concentration or iron, zinc and/or cobalt concentration in this outer region is at least 1.5 times, preferably at least twice and especially preferably at least 2.5 times as high as the corresponding concentration of these elements in the middle region which makes up the remaining region of the geometric equivalent diameter of the catalyst particle. More preferably, the gold is present to an extent of more than 90% in this outer region.

The determination and analysis of the distribution of the concentrations of gold and/or iron, zinc and/or cobalt across the catalyst particle profile can be effected, for example, by the embedding of the particles into a polymer matrix, subsequent polishing and then SEM-EDX analysis. An analogous analysis method by means of x-ray microanalysis (EPMA) is described, for example, in EP 2 210 664 A1 on page 18.

Preferably, the catalyst particles have a mean geometric equivalent diameter between 1 and 1000 μm, preferably between 10 and 250 μm and more preferably between 25 and 200 μm. The thickness of the outer region is preferably between 2 and 100 μm, preferably between 5 and 50 μm. The size of the geometric equivalent diameter is stated because the particles need not necessarily be in entirely spherical form, but may quite possibly also have more complex forms. Preferably, however, the particles are in virtually or ideally spherical form.

More preferably, gold and/or gold oxide- and metal oxide-containing, especially cobalt oxide-containing, particles having a mean diameter between 1 and 20 nm, preferably 2 and 10 nm, are present in the outer region of the catalyst particle. According to the production method, it is possible in accordance with the invention that the gold is present either in the form of pure particles or in a mixed form, for example together with the cobalt oxide. In this latter case, the gold is generally mixed only with a portion of the cobalt oxide. In addition, it is optionally also possible in both embodiments that the gold or gold-containing particles, for stabilization, are additionally provided with a thin layer, for example of $SiO_2$ and/or $Al_2O_3$. Equally preferably, the catalyst particles of the invention are porous. In this case, the porosity generally does not relate to the gold or gold-containing phases. Such porous catalyst particles have a specific surface area between 100 and 300 $m^2/g$, preferably between 150 and 250 $m^2/g$. In addition, the average pore diameter is generally 1 to 50 nm, preferably 2 to 20 nm.

Preferably, the ratio of the mass of catalyst to the liquid reaction mixing volume in the reactor is between 0.01 and 0.3 kg/l.

The reaction temperature is preferably between 60 and 100° C., more preferably between 70 and 95° C. The internal reactor pressure is preferably between 1 and 20 bar, more preferably between 2 and 10 bar.

The molar ratio between the steady-state concentrations of the alkyl alcohol and the methacrolein is more preferably between 4:1 and 15:1, especially preferably between 4.5:1 and 14:1 and most preferably between 5:1 and 13:1. The molar ratio between the steady-state concentrations of the alkyl alcohol and the methacrolein is even more preferably between 4:1 and 9.8:1, and very especially preferably between 4.5:1 and 9.5:1.

Particular preference is given to an execution of the present process in which the partial oxygen pressure in the reactor, or in the individual reactors at the point at which offgas is withdrawn, is between 0.01 and 0.8 bar, and in the gas mixture fed to the reactor is less than 5 bar.

Equally preferably, in addition to this or independently thereof, the steady-state methacrolein concentration in the reactor, or in the individual reactors, is between 1% and 21% by weight, more preferably between 3% and 21% by weight, most preferably between 5% and 20% by weight.

Most preferably, the alkyl alcohol is methanol and the alkyl methacrylate is methyl methacrylate.

Reactors used are preferably slurry reactors. In the case of a series connection of two or more reactors, it is also possible to combine various kinds of reactors with one another.

Preferably, reaction mixture is discharged continuously from the reactor and the catalyst remains in the reactor. In an illustrative embodiment, the reaction mixture is filtered through at least one filter, preferably within the particular reactor. Here too, the catalyst remains in the reactor after the filtration.

Alternatively, the reaction mixture is discharged continuously from the reactor and filtered through at least one filter, for example an external filter. Likewise preferably, the catalyst is passed back into the reactor after the filtration. For this purpose, continuously operable filters which can optionally be backflushed are used, which are preferably within the reactor, more preferably at the periphery in the upper portion of the reactor. Thereafter, the catalyst is optionally subjected to further treatment after the filtration and passed partly or completely back into the reactor. This further treatment may, for example, involve washing, reactivating or separation by particle size.

The filter porosity used with preference is between 5 and 100 micrometres, more preferably between 10 and 50 micrometres. For additional retention of the fine catalyst particles, the reaction mixture, once it has been filtered through reactor filters, is preferably filtered at least once more through finer filters having porosity of 1 to 10 μm outside the reactor, such that the particles of not more than 5 μm are retained by the filter to an extent of at least 90%.

Upstream of such filters, it is preferably possible to install an additional sedimentation system, for example at the periphery of the reactor as well. This may be a specific zone with laminar flow, where a majority of the catalyst used is sedimented. Such sedimentation is thus effected before the actual filtration.

It is advantageous when the reaction mixture, after being withdrawn continuously from the reactor, is worked up in at least one distillation column, and the alkyl alcohol and methacrolein are separated off as distillate and returned to the reactor.

Preferably, the gas required for the reaction is metered in in the finely dispersed state via gas distributors, called spargers, in the lower reactor portion. Preferably, the gas used is metered in in the direction toward the reactor base, in order that a minimum level of blockage with the catalyst particles can occur.

Apart from the reactants required for the reaction, various auxiliaries can be supplied to the process, for example acids, bases, polymerization inhibitors, antifoams, etc.

DRAWINGS

The FIGURE shows the experimental results from Table 2 further down expressed in the form of a graph. More particularly, what is shown here is the dependence of the space-time yield and of the selectivity of the reaction on the $O_2$ concentration.

EXAMPLES

The Catalyst Preparation

A 250 ml beaker is initially charged with 21.36 g of $Mg(NO_3)_2 \cdot 6H_2O$ and 31.21 g of $Al(NO_3)_3 \cdot 9H_2O$ together, which are dissolved in 41.85 g of demineralized water while stirring with a magnetic stirrer. Thereafter, 1.57 g of 60% $HNO_3$ are added while stirring. 166.67 g of silica sol (Köstrosol 1530AS from Bad Köstritz, 30% by weight of $SiO_2$, median size of the particles: 15 nm) are weighed into a 500 ml three-neck flask and cooled to 15° C. while stirring. 2.57 g of 60% $HNO_3$ are added gradually to the sol while stirring. At 15° C., the nitrate solution is added to the sol within 45 min while stirring. After the addition, the mixture is heated to 50° C. within 30 min and stirred at this temperature for a further 24 h. After this time, the mixture is spray-dried at exit temperature 130° C. The dried powder (spherical, median particle size 60 μm) is heated in a thin layer in a Naber oven to 300° C. within 2 h, kept at 300° C. for 3 h, heated to 600° C. within 2 h and finally kept at 600° C. for 3 h.

A suspension of 10 g of the $SiO_2$—$Al_2O_3$—MgO support from the preceding paragraph in 33.3 g of demineralized water is heated to 90° C. and stirred at this temperature for 15 min. Added to this suspension while stirring is a solution, heated to 90° C. beforehand, of $HAuCl_4*3H_2O$ (205 mg) and $Ni(NO_3)_2*6H_2O$ (567 mg, 1.95 mmol) in 8.3 g of water. After the addition, the mixture was stirred for a further 30 min, then cooled, filtered at room temperature, and subsequently washed six times with 50 ml each time of water. The material was dried at 105° C. for 10 h, finely crushed with a mortar and pestle, then heated from 18° C. up to 450° C. within 1 h and calcined at 450° C. for 5 h.

Comparative Examples 1 to 5

Gold-containing catalyst (for amount see Table 1) from the preceding description was continuously tested in a stirred pressure reactor with a stirrer that draws in gas with a reaction mixing volume of 200 ml at pressure 5 bar. In the course of this, a feed composed of 41% by weight of methacrolein (MAL hereinafter) and 59% by weight of methanol (44 g/h), and also a 0.5-1.0% by weight NaOH solution in methanol (7.3 g/h), were introduced continuously into the reactor. Air was utilized as oxygen source and was metered directly into the liquid reaction mixture. The offgas was cooled at −20° C. downstream of the reactor and the oxygen content therein was measured continuously. The amount of air introduced into the reactor was adjusted such that the oxygen concentration in the offgas was 4.0% by volume. After filtration, the liquid product mixture was discharged continuously from the reactor, cooled down and analyzed by means of gas chromatography (GC).

TABLE 1

| Ex. | Mass of cat. [g] | MAL conc. [wt %] | MeOH/MAL in reactor [mol/mol] | C(MAL) [%] | S(MMA) [%] | STY (max) [mol/kg ct-h] | TOS to deactivation >10% |
|---|---|---|---|---|---|---|---|
| CE1 | 5 | 22.3 | 5.6 | 35.3 | 86.0 | 16.1 | 100 h |
| CE2 | 10 | 12.9 | 9.8 | 56.4 | 91.1 | 14.2 | 500 h |
| CE3 | 15 | 10.0 | 12.2 | 66.2 | 94.8 | 10.6 | >1000 h |
| CE4 | 20 | 8.2 | 14.0 | 72.5 | 96.1 | 8.8 | >1000 h |
| CE5 | 25 | 6.9 | 16.6 | 76.7 | 96.0 | 7.5 | >1000 h |

Ex.: Example; CE: Comparative Example; conc.: concentration; C: conversion; S: selectivity; STY: space-time yield; TOS: time on stream As can be seen, the process can be conducted at the set oxygen concentration of 4% by volume with a good selectivity and long time on stream only when the molar ratio of methanol to MAL is greater than 10.

Comparative Examples 6 to 16 ($O_2$ Content)

Gold-containing catalyst (20 g) from the preceding description was tested as described in the comparative examples above. The only variation was the adjustment of the oxygen concentration in the offgas, which was varied between 1.9% and 6.6% by volume. Further process parameters and results are listed in Table 2.

TABLE 2

| Example | $O_2$ in the offgas [mol %] | MAL conc. in reactor [wt %] | MeOH/MAL in reactor [mol/mol] | C(MAL) [%] | S(MMA) [%] | STY [mol/kg ct-h] |
|---|---|---|---|---|---|---|
| CE6 | 1.9 | 11.07 | 10.32 | 64.2 | 95.1 | 7.6 |
| CE7 | 2.2 | 10.44 | 10.94 | 65.9 | 95.1 | 7.9 |
| CE8 | 2.4 | 9.62 | 11.89 | 68.2 | 94.1 | 8.2 |
| CE9 | 2.8 | 8.59 | 12.97 | 71.2 | 93.8 | 8.4 |
| CE10 | 2.9 | 8.36 | 13.29 | 72.4 | 93.4 | 8.4 |
| CE11 | 3.0 | 9.01 | 12.52 | 70.1 | 93.2 | 8.5 |
| CE12 | 3.6 | 8.19 | 14.20 | 72.5 | 93.5 | 8.6 |
| CE13 | 4.0 | 8.29 | 14.04 | 72.2 | 92.0 | 8.6 |
| CE14 | 5.9 | 7.54 | 15.51 | 74.0 | 92.2 | 8.6 |
| CE15 | 6.1 | 8.13 | 14.49 | 72.2 | 93.4 | 8.6 |
| CE16 | 6.6 | 8.55 | 13.84 | 72.2 | 90.4 | 8.5 |

It can be seen from these experiments that, with a relatively high methanol content compared to the steady-state MAL concentration, the space-time yield increases up to an $O_2$ concentration of about 3% by volume and beyond that is apparently no longer dependent thereon. The selectivity, by contrast, appears to decrease slightly with rising $O_2$ concentration. This relationship is additionally depicted in the FIGURE.

With an $O_2$ concentration above 6% by volume, more particularly, relatively rapid deactivation of the catalyst and an associated reduction in STY were observed. The overall finding was that a rising $O_2$ concentration has an adverse effect on the catalyst time on stream.

Moreover, it can be clearly seen from the series of experiments that the selectivity of the reaction, S(MMA), reduces with rising $O_2$ offgas concentration. The reason for the loss of selectivity and catalyst deactivation in the region of higher $O_2$ concentrations is probably attributable to the formation of oligo- and polymers of methacrolein.

It can be seen from the dependence of the space-time yield STY on the $O_2$ concentration that the reaction is limited by oxygen supply at relatively low $O_2$ contents, whereas, over and above a particular $O_2$ concentration (in this case between 3% and 4% by volume), there is no longer any apparent dependence, and so a further increase in the $O_2$ concentration does not result in any further increase in the STY.

A preferred implementation of the oxidative esterification in the range of kinetic limitation by oxygen supply is thus advantageous; in other words, with a slight deficiency of $O_2$, the latter is used up rapidly for the reaction without increasing by-product formation (for example by polymerization). In an oxygen excess (in this case with more than 4% by volume of $O_2$ in the offgas), by contrast, there are higher amounts and concentrations of free oxygen in the reaction mixture, which promotes by-product formation through polymerization.

Examples 1 to 10 and Comparative Example 17 (Variation in the Methanol/MAL Concentrations)

Gold-containing catalyst (20 g) from the preceding description was tested analogously to the comparative examples above, but here with an oxygen concentration of 2.0% by volume in the offgas. A constant amount of feed of MAL and methanol (45 g/h, see table below for MAL concentration) and 0.5% to 1% by weight of NaOH in methanol (7.6 g/h) was introduced continuously into the reactor. Results are shown in Table 3.

TABLE 3

| Ex. | MAL in feed [wt %] | MeOH in feed [wt %] | MAL conc. in reactor [wt %] | MeOH/MAL in feed [mol/mol] | MeOH/MAL in reactor [mol/mol] | Ratio reactor/ FEED | C(MAL) [%] | S(MMA) [%] | STY [mol/kg ct-h] |
|---|---|---|---|---|---|---|---|---|---|
| 10 | 40.06 | 59.94 | 11.07 | 3.27 | 10.32 | 3.15 | 64.2 | 94.3 | 7.62 |
| 1 | 41.54 | 58.46 | 11.65 | 3.08 | 9.48 | 3.08 | 63.5 | 94.3 | 7.83 |
| 2 | 41.24 | 58.76 | 12.39 | 3.12 | 8.84 | 2.84 | 61 | 94.5 | 7.43 |
| 3 | 41.85 | 58.15 | 12.64 | 3.04 | 8.70 | 2.86 | 60.7 | 94.4 | 7.53 |
| 4 | 42.81 | 57.19 | 13.98 | 2.92 | 7.79 | 2.67 | 57.8 | 94.3 | 7.41 |
| 5 | 44.2 | 55.80 | 16.34 | 2.76 | 6.33 | 2.29 | 53.7 | 94.6 | 7.05 |
| 6 | 44.7 | 55.30 | 16.51 | 2.71 | 6.46 | 2.39 | 53.2 | 94.8 | 7.09 |
| 7 | 47.76 | 52.24 | 20.1 | 2.39 | 5.09 | 2.13 | 48.1 | 94.4 | 6.91 |
| 8 | 47.74 | 52.26 | 19.88 | 2.39 | 5.09 | 2.13 | 48.2 | 92.8 | 6.70 |
| 9 | 47.85 | 52.15 | 20.48 | 2.38 | 4.98 | 2.09 | 46.8 | 91.4 | 6.36 |
| CE17 | 49.7 | 50.30 | 23.76 | 2.21 | 3.96 | 1.79 | 41.8 | 90.0 | 6.01 |

The steady-state ratio of alkyl alcohol to methacrolein in the reactor to the ratio of the substances in the feed in the steady state, in the experiments listed in Table 3, is between 1.5 and 3.5.

As can be seen, the esterification reaction can surprisingly be conducted without any problem and with high selectivity even with a lower molar ratio of methanol to MAL if a relatively low oxygen concentration in the offgas (2% by volume) was set.

Examples 11 and 12 (Long-Term Test)

Gold-containing catalyst (20 g) from the preceding description was continuously tested in a stirred pressure reactor with a stirrer that draws in gas with a reaction mixing volume of 200 ml at pressure 5 bar. In the course of this, a feed composed of 44.5% by weight of MAL and 55.5% by weight of methanol (44 g/h), and also a 1.0% by weight NaOH solution in methanol (7.3 g/h), were introduced continuously into the reactor. Air was utilized as oxygen source and was metered directly into the liquid reaction mixture. The offgas was cooled at −20° C. downstream of the reactor and the oxygen content therein was measured continuously. The amount of air introduced into the reactor was adjusted such that the oxygen concentration in the offgas was 2.0% by volume. After filtration, the liquid product mixture was discharged continuously from the reactor, cooled down and analyzed by means of GC.

| Ex. | Run time [h] | MAL in feed [wt %] | MAL conc. in reactor [wt %] | MeOH/MAL in reactor [mol/mol] | C(MAL) [%] | S(MMA) [%] | STY [mol/kg ct-h] |
|---|---|---|---|---|---|---|---|
| 11 | 500 | 44.5 | 16.5 | 6.5 | 53.2 | 94.8 | 7.09 |
| 12 | 2000 | 44.5 | 16.6 | 6.5 | 53.0 | 94.8 | 7.06 |

As can be seen, the esterification reaction here too can surprisingly be conducted without any problem over a prolonged period with high selectivity even with a lower molar ratio of methanol to MAL if a relatively low oxygen concentration in the offgas was set.

The invention claimed is:

1. A process, comprising: continuously performing a reaction for oxidative esterification of methacrolein with an alkyl alcohol and oxygen to produce an alkyl methacrylate in the presence of a gold catalyst in a reactor system comprising a reactor, the reactor comprising a gas feed and offgas outlet, wherein a molar ratio of the alkyl alcohol at a steady-state concentration to the methacrolein at a steady-state concentration in the reactor is less than 10:1, an oxygen concentration in a gas phase at the offgas outlet in the reactor is less than 4.5% by volume, a steady-state molar ratio of the alkyl alcohol to the methacrolein in the reactor to a steady-state molar ratio of the alkyl alcohol to the methacrolein in the gas feed is between 1.5 and 15, and a steady-state concentration of the methacrolein in the reactor is less than 21% by weight.

2. The process according to claim 1, wherein the molar ratio of the alkyl alcohol at a steady-state concentration to the methacrolein at a steady-state concentration in the reactor is between 4:1 and less than 10:1, the steady-state molar ratio of the alkyl alcohol to the methacrolein in the reactor to the steady-state molar ratio of the alkyl alcohol to the methacrolein in the gas feed is between 1.8 and 15, and the steady-state concentration of the methacrolein in the reactor is less than 15% by weight.

3. The process according to claim 1, wherein the molar ratio of the alkyl alcohol at a steady-state concentration to the methacrolein at a steady-state concentration in the reactor is between 5:1 and less than 9.5:1, the steady-state molar ratio of the alkyl alcohol to the methacrolein in the reactor to the steady-state molar ratio of the alkyl alcohol to the methacrolein in the gas feed is between 2 and 13, and the steady-state concentration of the methacrolein in the reactor is less than 12% by weight.

4. The process according to claim 1, wherein the catalyst is in the form of catalyst particles comprising oxygen, silicon, aluminium, at least basic element, gold and optionally one of nickel, cobalt, iron and zinc, wherein the at least one basic element is an alkali metal, an alkaline earth metal, a rare earth metal or mixtures of these metals.

5. The process according to claim 1, wherein a reaction temperature is between 60 and 100° C. and an internal reactor pressure is between 1 and 20 bar.

6. The process according to claim 5, wherein the reaction temperature is between 70 and 95° C. and the internal reactor pressure is between 2 and 10 bar.

7. The process according to claim 1, wherein a partial oxygen pressure at the offgas outlet in the reactor is between 0.01 and 0.8 bar, and a partial oxygen pressure in a gas mixture fed to the reactor is less than 10 bar.

8. The process according to claim 1, wherein the steady-state concentration of the methacrolein in the reactor is 3% or more and less than 21% by weight.

9. The process according to claim 8, wherein the steady-state concentration of the methacrolein in the reactor is between 5% and 20% by weight.

10. The process according to claim 1, wherein the alkyl alcohol is methanol and the alkyl methacrylate is methyl methacrylate.

11. The process according to claim 1, wherein a ratio of a mass of the catalyst to a liquid reaction mixing volume in the reactor is between 0.01 and 0.3 kg/l.

12. The process according to claim 1, wherein the reactor is a slurry reactor.

13. The process according to claim 1, wherein a reaction mixture is discharged continuously from the reactor and the catalyst, after being separated off, remains in the reactor.

14. The process according to claim 1, wherein a reaction mixture, after being withdrawn continuously from the reactor, is worked up in at least one distillation column, and the alkyl alcohol and methacrolein are separated off as distillate and returned to the reactor.

15. The process according to claim 1, wherein the oxygen concentration in the gas phase at the offgas outlet in the reactor is less than 3.0% by volume.

16. The process according to claim 3, wherein the steady-state molar ratio of the alkyl alcohol to the methacrolein in the reactor to the steady-state molar ratio of the alkyl alcohol to the methacrolein in the gas feed is between 1.5 and 3.5.

* * * * *